(12) United States Patent
Abry

(10) Patent No.: US 8,608,707 B2
(45) Date of Patent: *Dec. 17, 2013

(54) AUTOINJECTOR WITH ROTATABLE DESHIELDER FOR AXIALLY DISPLACING A NEEDLE SHIELD

(71) Applicant: Becton Dickinson France, Le Pont de Claix (FR)

(72) Inventor: Herve Abry, Echirolles (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/659,210

(22) Filed: Oct. 24, 2012

(65) Prior Publication Data

US 2013/0053787 A1   Feb. 28, 2013

Related U.S. Application Data

(63) Continuation of application No. 12/679,687, filed as application No. PCT/IB2007/003957 on Sep. 25, 2007, now Pat. No. 8,313,470.

(51) Int. Cl.
    *A61M 5/32*       (2006.01)
(52) U.S. Cl.
    USPC .......................................... 604/198

(58) Field of Classification Search
    USPC ................. 604/110, 187, 192, 193, 197, 198
    See application file for complete search history.

(56) References Cited

U.S. PATENT DOCUMENTS

| 8,313,470 B2 * | 11/2012 | Abry .............................. 604/198 |
| 2004/0225262 A1 | 11/2004 | Fathallah et al. |
| 2010/0094214 A1 * | 4/2010 | Abry et al. .................... 604/110 |

FOREIGN PATENT DOCUMENTS

WO    01/24855 A1    4/2001

* cited by examiner

*Primary Examiner* — Nicholas Lucchesi
*Assistant Examiner* — Nathan R Price
(74) *Attorney, Agent, or Firm* — Hoffmann & Baron, LLP

(57) ABSTRACT

The invention relates to an automatic injection device including a container provided with a needle; a housing receiving a container movable relative to the housing between an initial position to an insertion position; a needle shield for receiving the needle and in which the needle is embedded prior to use of the device; and a deshielder coupled to the needle shield by a first connecting arrangement and removably assembled to the distal part of the housing by a second connecting arrangement. The first and second connecting arrangements are designed so that a rotational movement of the deshielder about the device axis of the device with respect to the housing causes an axial displacement of the needle shield in the distal direction with substantially no rotational movement of the needle shield with respect to the needle.

16 Claims, 4 Drawing Sheets

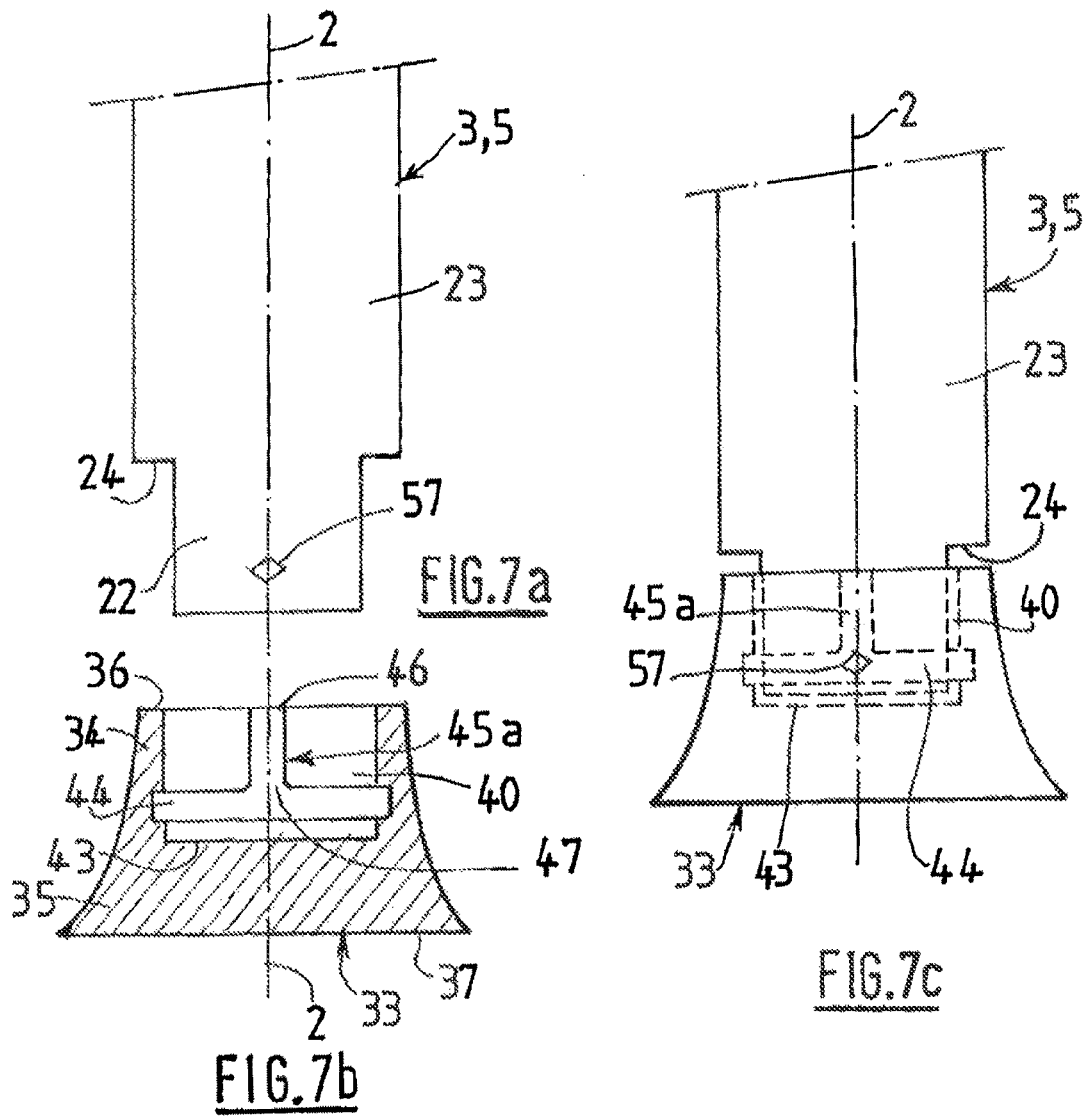
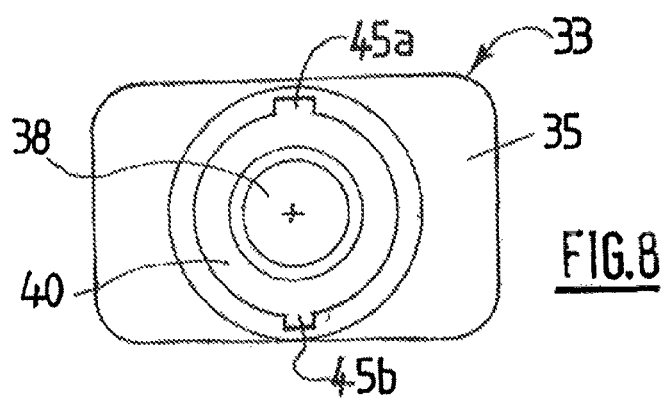

AUTOINJECTOR WITH ROTATABLE DESHIELDER FOR AXIALLY DISPLACING A NEEDLE SHIELD

CROSS-REFERENCES TO RELATED APPLICATIONS

This application is a continuation of U.S. application Ser. No. 12/679,687, filed Jul. 6, 2010, now allowed, which is a National Stage Application under 35 U.S.C. §371 of PCT Application No. PCT/IB2007/003957, filed Sep. 25, 2007, the entire contents of these applications being incorporated by reference herein.

BACKGROUND OF THE INVENTION

The present invention relates to a device for automatic injection of a product in a very safe way, especially for self-injection.

In this application, the device has a longitudinal axis which is the main axis of the constitutive parts of said device. The distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

The injection devices of the prior art are usually provided with needle shields that are made of rubber or elastomeric material. A drawback of these devices is that the sharp needle, embedded into the rubber shield, may create a core of rubber if rotated when removed. Then, this rubber core, located into the needle internal diameter, may then block the needle and prevent the drug to be injected or may be injected into the patient's skin together with the drug upon activation of the injection device.

It would therefore be of interest to provide an injection device having an appropriate needle shield that does not jeopardize the quality of the injection when it is removed from the injection device before use.

Some injection devices of the prior art comprise a deshielder which is initially coupled to said needle shield and removably assembled to the distal part of a housing of the injection device. The deshielder is intended to be removed from said housing prior to use of said device, thereby also removing the needle shield. To avoid the creation of the rubber core, the deshielder and the housing are usually provided with connecting means designed to make it impossible to rotate the deshielder with respect to the housing, which would entail the rotation of the needle shield with respect to the needle and, consequently, the creation of such a rubber core. In other words, the only possibility for the patient to remove the needle shield, by means of the deshielder, is to pull the deshielder axially. This arrangement has a number of drawbacks.

First of all, the straight pulling movement is quite difficult to perform, especially for elder or arm and hand impaired people, because this movement requires a certain force and uses both hands and forearms.

Moreover, in the first instance, many users may tend to turn the deshielder instead of pulling it axially, since the removal of caps is generally performed through a rotational movement. Consequently, these users may be confused when realizing that the deshielder cannot be removed in this way, and may take time to try to pull the deshielder axially in order to remove it.

Consequently, there is a need for self-injection devices provided with a needle shield and a deshielder that could be removed by a rotational movement with no risk to create a rubber core in the needle.

Besides, there is also a need for such a self-injection device that would also allow a patient used to known devices to remove the deshielder by pulling it axially.

SUMMARY OF THE INVENTION

The present invention meets this need by proposing a device for automatic injection of a product into an injection site, said device having a longitudinal axis and comprising:
 a housing capable of receiving a container movable relative to said housing between an initial position, in which a tip of a needle provided on the container does not extend beyond a distal end of said housing, to an insertion position, distally spaced relative to said initial position and in which the tip of the needle extends beyond said distal end of said housing;
 a needle shield for receiving said needle and in which the needle is embedded prior to use of said device;
 a deshielder coupled to said needle shield by first connecting means and removably assembled to the distal part of the housing by second connecting means, the deshielder being intended to be removed from said housing, thereby also removing the needle shield, prior to use of said device;
 characterized in that:
 said first and second connecting means are designed so that a rotational movement of the deshielder about the device axis with respect to the housing causes an axial displacement of the needle shield in the distal direction with substantially no rotational movement of the needle shield with respect to the needle.

Thanks to this arrangement, a patient can remove the needle shield and the deshielder by using a rotational movement, i.e. a movement which is both easy to perform and natural, without any risk to create a rubber core in the needle.

In an embodiment of the invention, the second connecting means are designed to allow a rotational movement of the deshielder about said axis with no possible simultaneous axial translation of the deshielder, and the first connecting means comprise:
 axial retaining means designed to prevent the needle shield from moving axially in the proximal direction and to cause the needle shield to move axially in the distal direction, when the deshielder is turned about the device axis with respect to the housing;
 and helical means designed to convert the rotational movement of the deshielder about the device axis with respect to the housing into an axial displacement of the needle shield in the distal direction with respect to the needle.

In this embodiment, the movement implemented by the patient is similar to an unscrewing movement, which has to be performed clockwise or anticlockwise depending on the helical means geometry.

The second connecting means can be designed to also allow an axial displacement of the deshielder in the distal direction with respect to the housing with no possible simultaneous rotation of the deshielder, this axial displacement causing the axial removal of both the deshielder and the needle shield off the housing. As a consequence, even with the above mentioned connecting means designed to allow a rotational movement of the deshielder, it is still possible for the patient to remove said deshielder by pulling it axially, if this movement is more convenient or more usual for him/her.

In one embodiment, the deshielder comprises a cylindrical through-hole having an axis substantially identical to the device axis and an internal thread, and the first connecting means comprise a hollow sheath receiving the needle shield therein with substantially no possible rotation therebetween, said sheath being mounted in the through-hole, said sheath being further provided with an external thread corresponding to the through-hole internal thread and with axial retaining means cooperating with the needle shield so that a displacement of the first connecting means in the distal direction causes a displacement of the needle shield in the distal direction.

In order to achieve a cooperation between the sheath and the needle shield with substantially no possible rotation, it is possible to use materials providing a high coefficient of friction between the sheath and the needle shield and a low coefficient of friction between the sheath and the deshielder.

The axial retaining means can comprise at least one radially extending tongue projecting from the proximal end of the sheath and abutting onto the proximal end of the needle shield. The tongue may be a localized projection or may be a continuous projection extending along the whole periphery of the sheath, forming an annular collar.

Preferably, the axial retaining means are abutting onto the distal end of the container prior to use of said device. In this way, the axial displacement of the sheath in the proximal direction is prevented, and consequently the needle shield cannot move axially in the proximal direction.

For example, the deshielder comprises an annular housing, coaxial with the needle and having an internal diameter larger than the needle shield external diameter, said annular housing receiving a distal portion of the housing. Thus, the invention provides guiding means designed to allow the axial translation and/or the rotation of the deshielder with respect to the housing.

In that case, the annular housing can have an internal diameter larger than the through-hole external diameter.

Preferably, the annular housing comprises on one of its longitudinal walls a circular groove located in a plan substantially orthogonal to the device axis, and in that the distal portion of the housing comprises a bump intended to be inserted in said groove. Therefore, an axial displacement of the deshielder with respect to the housing is impossible simultaneously with the rotational movement of the deshielder with respect to the housing.

The annular housing can further comprise on said longitudinal wall at least one axial slot the proximal end of which comes out at the proximal end of the deshielder annular housing and the distal end of which comes out into said circular groove, the bump provided on the housing distal portion being designed to slide into said slot. As a consequence, it is possible for a user to remove the deshielder by pulling it axially, provided the bump is located in line with the axial slot.

Preferably, said longitudinal wall of the annular housing comprises two diametrically opposed axial slots.

The device can also comprise means designed to ensure that, prior to use of said device, the bump is located in the annular groove, at the distal end of one axial slot. Therefore, two movements are possible to remove the deshielder: the user can pull it axially or make it rotate with respect to the body. Moreover, after a half-turn rotational movement, the user can complete the deshielder removal by pulling it axially.

In an advantageous embodiment, the deshielder comprises ergonomic means to make its removal off the housing easier for a patient.

For example, the ergonomic means comprise ribs provided on the external surface of the deshielder and extending substantially axially and/or radially. Alternatively or additionally, the deshielder can have an enlarged distal part: This non cylindrical shape facilitate the pulling movement.

The device can further comprise tamper-evidence means provided between the housing and the deshielder prior to use of the device, such as breakable bridges.

In one embodiment, said first and second connecting means are designed so that a rotational movement of the deshielder about the device axis of 360° at most causes an axial displacement of the needle shield enough so that the needle is not embedded in the needle shield any more. Preferably, a rotational movement of the deshielder about the device axis of 180° is sufficient to that end.

The device can also comprise means for limiting the rotation of the deshielder with respect to the housing to around 180°. This arrangement may be very convenient for the patient, especially when the longitudinal wall of the annular housing comprises two diametrically opposed axial slots: in this case, if the bump is initially located in line with a first slot, after a half-turn rotation of the deshielder, the bump is located in line with the opposite slot. Consequently, the deshielder can then be pulled straight to be completely removed from the housing.

BRIEF DESCRIPTION OF THE DRAWINGS

The device of the invention will now be further described in reference to the following description and attached drawings in which:

FIGS. 7a and 7b are schematic longitudinal cross sections of the housing and the deshielder, respectively, and FIG. 7c schematically shows these components when assembled, prior to use of the device;

FIG. 8 is a top view of the deshielder of the device of FIG. 1.

DETAILED DESCRIPTION OF THE INVENTION

Figure 1:
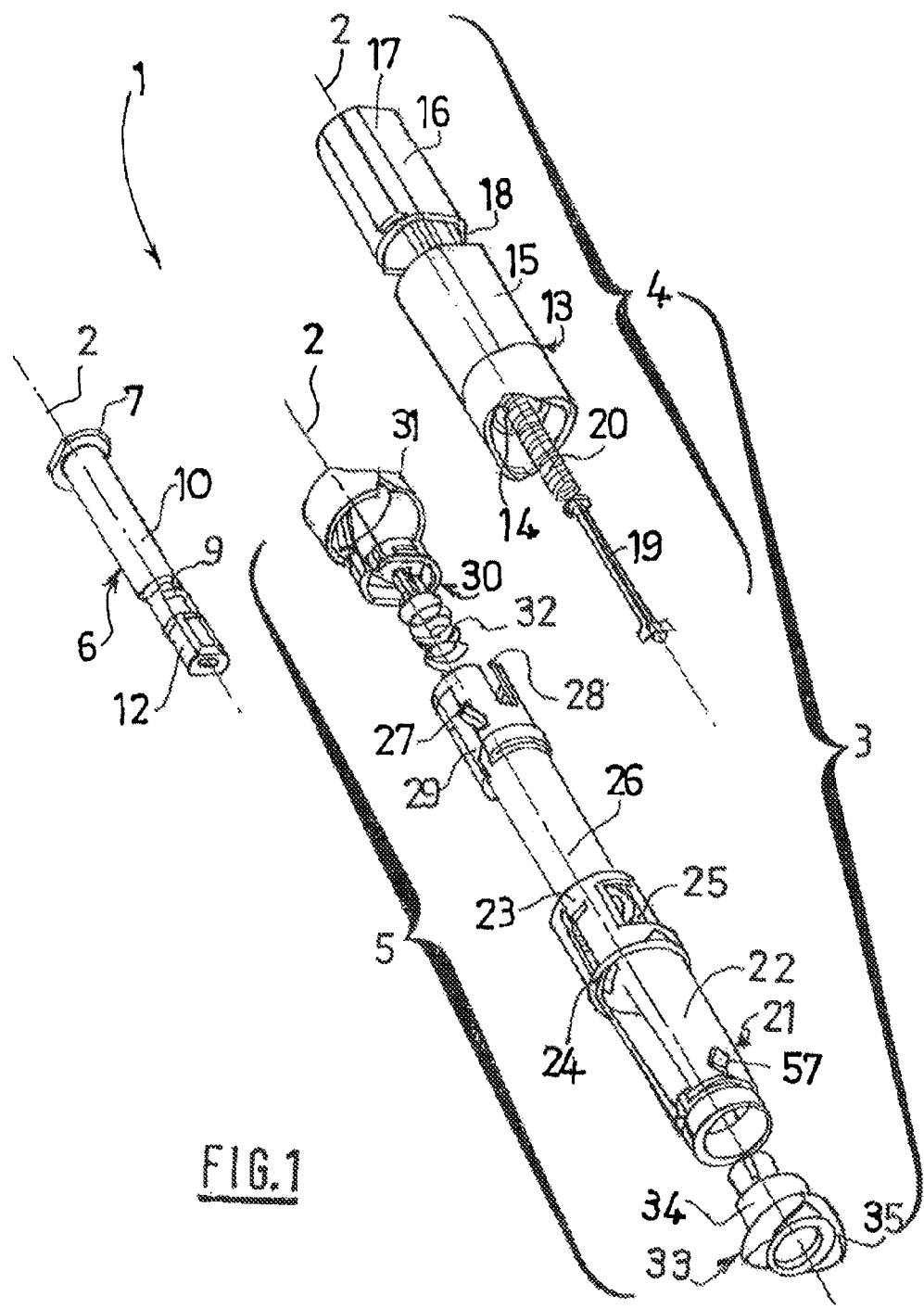
FIG. 1 is an exploded perspective view of an embodiment of the device of the invention.

Referring now to the drawings, the present invention will now be described in detail. FIG. 1 shows an exploded perspective view of a device for automatic injection according to an embodiment of the present invention and generally designated by reference number 1. The device 1 has a longitudinal axis 2 which is the main axis of the constitutive parts of said device, as described below. It is generally made of plastics.

The device 1 comprises a housing 3 comprised of an upper body assembly 4 and a lower body assembly 5 that may be connected to each other by means of a snap-fit connection, screw-type connection, bayonet connection, or other means of connecting two parts together, in an unreleasable way or not.

A container 6 such as, for example, a syringe, is received in the housing 3, the container 6 being movable axially relative to said housing 3. Preferably, the container 6 is partially received in each of the upper and lower body assemblies 4, 5. The container 6 has a flange 7 defined at an open proximal end, and an injection needle 8 (see FIG. 2) at a substantially closed distal end 9. Lateral walls 10 extend between the proximal and distal ends and define a reservoir 11 sized and shaped to contain a predetermined amount of a product for injection. The injection needle 8 is in fluid communication with the reservoir 11 and provides an outlet port of the container 6 for the product.

A needle shield 12 is provided at the distal end of the container 6 to cover and protect the needle 8 before use of the device 1. The needle shield 12, which is generally made of natural or synthetic rubber material, also provides for a sealing means of the distal end of the container 6 before use. A piston (not shown) provided in the container 6 is movable within the reservoir 11, with respect to the container 6. The movement of the piston causes the product to be expelled from said container 6 through the needle 8 during the injection of the product into the patient.

The housing 3 illustrated in FIG. 1 is only one possible embodiment of a housing of a device according to the invention, and will be now briefly described.

The upper body assembly 4 has a generally cylindrically shaped outer sleeve 13 comprised of an inner cylinder 14 and an outer cylinder 15, the cylinders 14, 15 being linked to each other by at least a radial wall. A push button 16, received in the outer sleeve 13, has a proximal end closed by a transversal wall 17 which forms a pushing surface for the user to exert a manual pressure on said push button 16, and a distal open end 18. A plunger rod 19 for causing the piston to move with respect to the container 6 is received within the inner cylinder 14 of said outer sleeve 13 of the upper body assembly 4.

A first spring 20 is provided between said plunger rod 19 and said inner cylinder 14. Spring 20 causes displacement of the container 6 within the housing 3 from an initial position, in which a tip of the needle 8 does not extend beyond the distal end of the housing 3 (FIG. 2) to an injection position, distally spaced relative to said initial position and in which the tip of the needle 8 extends beyond said distal end of said housing 3 and is exposed over a predetermined length. Spring 20 further causes movement of the piston within the container 6 to cause the product to be expelled therefrom through the needle 8.

The lower body assembly 5 comprises a body 21 which receives at least partially the container 6. The body 21 has a general cylindrical shape and is open at both ends. The body 21 has a distal part 22 and a proximal part 23 of greater diameter, joined by a radial wall 24. Two opposite windows 25 are provided in the proximal part 23 of body 21.

The lower body assembly 5 also includes a safety shield 26 that is at least partially received within the body 21. A proximal part of the safety shield 26 is provided on its outer wall with two opposite flexible tongues 27 capable of being radially deflected. The proximal part of the safety shield 26 is also provided with two opposite first proximal teeth 28 and with two opposite second proximal teeth 29, distally spaced from said first proximal teeth 28.

The safety shield 26 is coupled to the body 21 and is able to move between a first position and a second position in which the tip of the needle does not extend beyond a distal end of the safety shield 26.

The device 1 further comprises an inner ring 30 which receives part of the proximal portion of said container 6, the inner diameter of said inner ring 30 being less than the outer diameter of the flange 7 of said container 6 so as to prevent to container 6 from passing completely through the ring 30 when ring 30 and container 6 are assembled together. When assembled together, the inner ring 30 and container 6 may move together within the upper and lower body assemblies 4, 5 as the container 6 is moved from its initial position to its insertion position.

The device 1 also comprises an outer ring 31 which receives, at least partially, said inner ring 30. A second spring 32 is provided between container 6 and inner ring 30.

The device 1 of the present invention is also provided with a deshielder 33 which carries the needle shield 12. Prior to use of the device 1, a user removes the deshielder 33, which also removes the needle shield 12. The deshielder 33 is coupled to the needle shield 12 by first connecting means and removably assembled to the distal part 22 of the body 21 by second connecting means, which will now be described in detail.

The deshielder 33 has a longitudinal axis 2, a proximal part 34 which is substantially cylindrical, and an enlarged distal part 35, which is rectangular-shaped when seen axially from the proximal end of the deshielder 33 (see FIG. 8). The deshielder 33 has a proximal end 36 and a distal end 37 that are substantially flat and perpendicular to the axis 2.

The deshielder 33 comprises a cylindrical through-hole 38 whose axis is the longitudinal axis 2, the wall 39 of said through-hole 38 having an internal thread. The deshielder 33 also comprises an annular housing 40, coaxial with the cylindrical through-hole 38 and arranged around it (the annular housing 40 having an internal diameter $D_{40}$ larger than the diameter $D_{38}$ of the through-hole 38, as shown on FIG. 2). The annular housing 40 comes out at the proximal end 36 of the deshielder 33 but not at the distal end 37 thereof. It has an internal cylindrical wall 41, an external cylindrical wall 42, and a bottom 43 substantially flat and orthogonal to the axis 2.

The annular housing 40 comprises on its external cylindrical wall 42 a circular groove 44 located in a plan substantially orthogonal to the axis 2 and preferably close to the bottom 43. Two diametrically opposed axial slots 45a, 45b are provided on said external cylindrical wall 42. The proximal end 46 of each slot 45a, 45b comes out at the proximal end 36 of the deshielder 33, and the distal end 47 of each slot 45a, 45b comes out into said circular groove 44.

Figure 4:
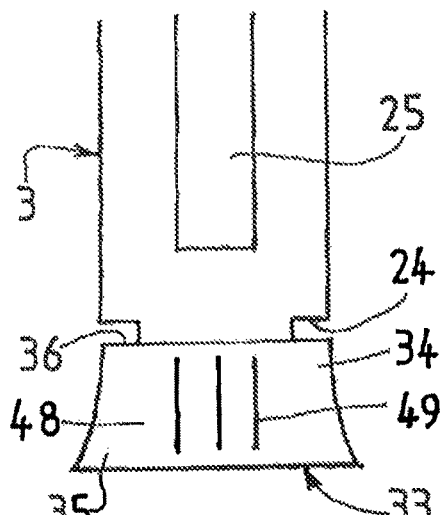
FIGS. 4 and 5 are partial perspective views of the device of FIG. 1, shifted of 90° the one with respect to the other, showing the ergonomic means to make the removal of the deshielder off the housing easier.
Figure 5:
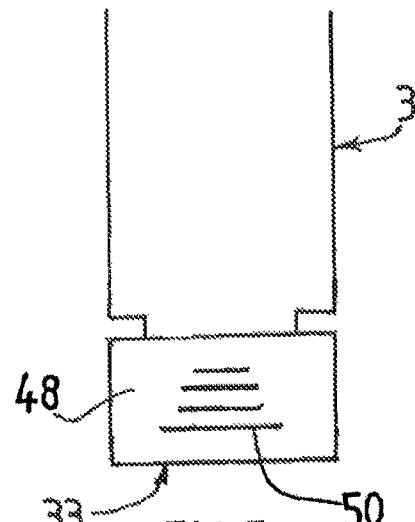
Figure 6A:
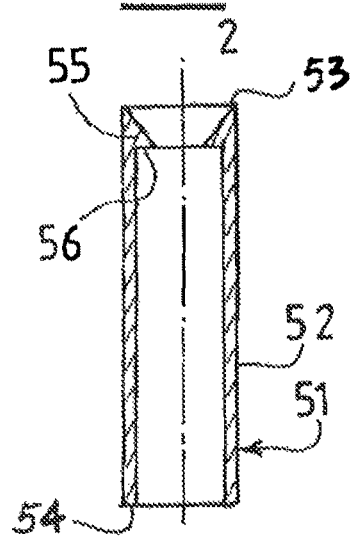
FIGS. 6a and 6b are schematic longitudinal cross sections of the sheath and the deshielder, respectively.
Figure 6C:
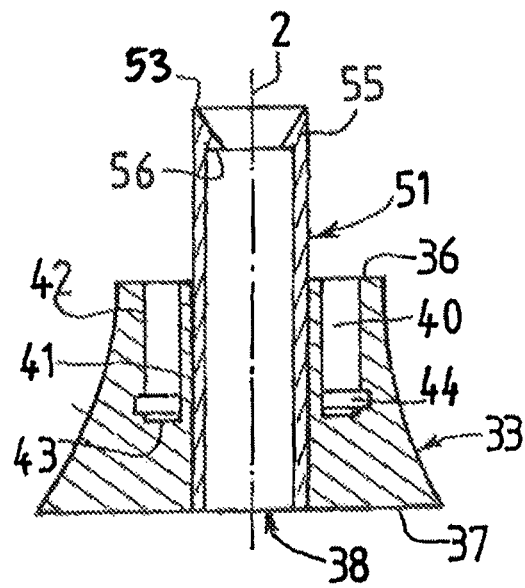
FIG. 6c is a schematic longitudinal cross section of these components when assembled, prior to use of the device.
Figure 6B:
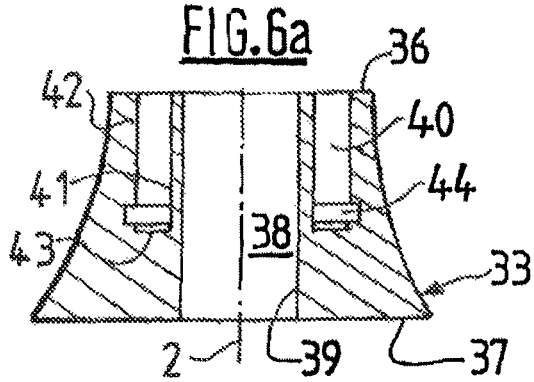

The deshielder 33 also has ribs provided on its external surface 48, namely axially extending ribs 49 and radially extending ribs 50, spaced from the axially extending ribs 49 at the periphery of the deshielder 33 (see FIGS. 4 and 5).

The device 1 comprises a hollow cylindrical sheath 51 having an internal diameter substantially identical to the diameter of the needle shield 12, so that the needle shield 12 can be received in the sheath 51 with substantially no possible rotation therebetween. The external wall 52 of the sheath 51 is provided with an external thread corresponding to the through-hole internal thread.

The sheath 51 has a proximal end 53 and a distal end 54, and its axial length is greater that the distance between the proximal and distal ends 36, 37 of the deshielder 33. The sheath 51 is provided in its proximal portion with axial retaining means consisting of a radially inwardly extending collar 55. having a radial wall 56.

Figure 2:
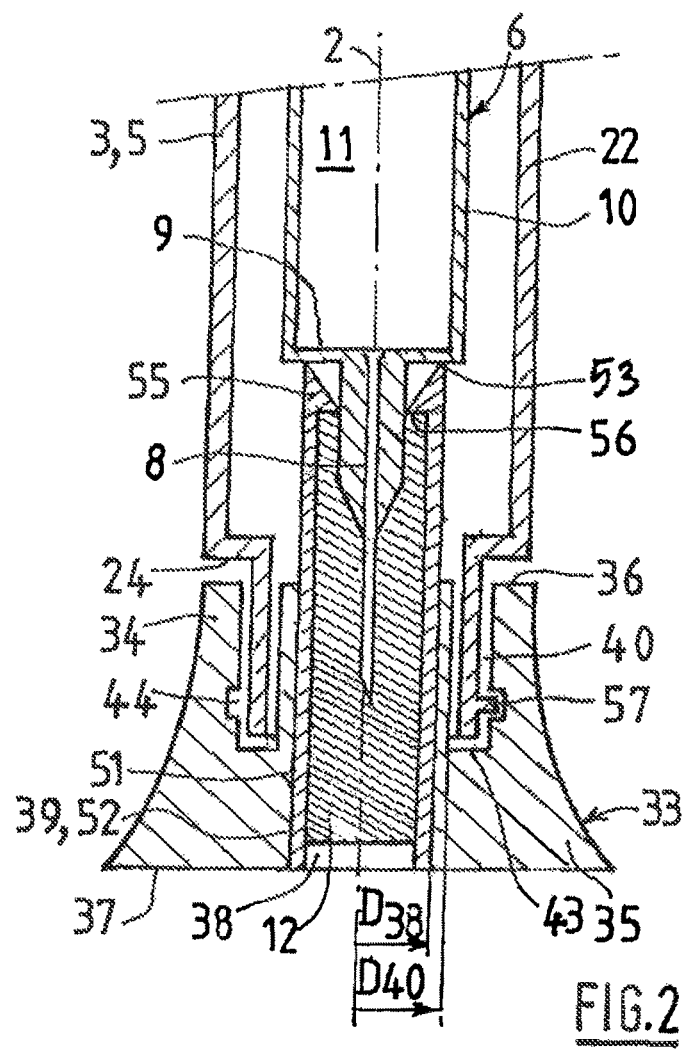
FIG. 2 is a longitudinal cross section of the device of FIG. 1.

As shown on FIG. 2, prior to use of the device 1, the sheath 1 is mounted in the through-hole 38 of the deshielder 33, the respective external and internal threads thereof being mutually engaged, and the distal end 54 of the sheath 51 and the distal end 37 of the deshielder 33 lying substantially in the same plane. The needle shield 12 is received in the sheath 51, the radial wall 56 of the collar 55 abutting onto the proximal end of the needle shield 12, and the proximal end 53 of the sheath 51 being in contact with the distal end 9 of container 6. The needle 8 is then embedded in the needle shield 12, which does not extend beyond the distal end 54 of the sheath 51.

Furthermore, the distal part 22 of the body 21 is received into the annular housing 40 of the deshielder 33, the distal end of body 21 being close to the bottom 43 of said annular housing 40, and the radial wall 24 being close to the proximal end 36 of the deshielder 33. It will be understood that the axial length of the annular housing 40 has to be size up according to the axial length of the distal part 22 of the body 21. In the illustrated embodiment, the annular housing 40 extends longitudinally over about half the distance between the proximal and distal ends 36, 37 of the deshielder 33.

The distal part 22 of the body 21 comprises a bump 57 intended to be inserted in said groove 44 and to slide into one of said slots 45a, 45b. Prior to use, the bump 57 is located in the groove 44, in line with one of the slots 45a.

Figure 3:
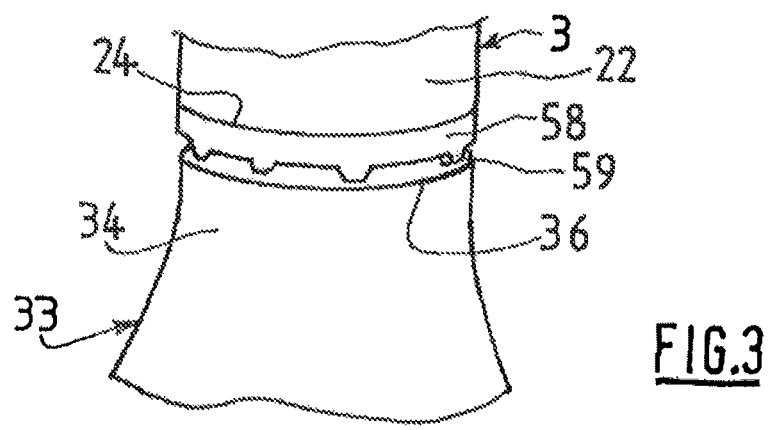
FIG. 3 is a partial perspective view of the device of FIG. 1, showing the tamper-evidence means provided between the housing and the deshielder.

As shown in FIG. 3, the device 1 can also comprise tamper-evidence means provided between the housing 3 and the deshielder 33 prior to use of the device 1. These tamper-evidence means can comprise a ring 58 and breakable bridges 59 connecting the radial wall 24 of the body 21 and the proximal end 36 of the deshielder 33. Once the deshielder 33 that carries the needle shield 12 has been removed, the tamper-evidence means are broken, and even if the deshielder 33 is placed back onto the housing 3, a patient will be aware of such a previous opening of the device 1. The device 1 may contain sterile drugs and it is important to prove to end users that the container has not been tampered, and that the drug sterility has been maintained until the point of use.

When a patient wants to use the device 1, he/she can either pull the deshielder 33 axially or turn it around the axis 2.

If the deshielder 33 is pulled axially, which is possible since the bump 57 is located in line with one slot 45a or 45b, the bump 57 slides into said slot 45a or 45b when the deshielder is moved away from the housing 3. During this movement, the bridges 59 are broken, which allows a further displacement of the deshielder 33 until it is completely removed. Because of the external thread of the sheath 51 cooperating with the internal thread of the through-hole 38, the sheath 51 and the deshielder 33 are integral during this axial displacement. Furthermore, because of the radial wall 56 of the collar 55 of the sheath 51 abutting on the proximal end of the needle shield 12, the axial removal of the deshielder 33 causes the axial displacement of the needle shield 12. Consequently, by pulling straight the deshielder 33, a patient can remove the deshielder 33 without any risk of creating a rubber core in the needle 8.

If the deshielder 33 is rotated about the axis 2 with respect to the housing 3, the bridges 59 are broken and the bump 57 is moved into the circular groove 44, so that the deshielder 33 is not moved away axially from the housing 3. However, because of the external thread of the sheath 51 cooperating with the internal thread of the through-hole 38, the sheath 51 is moved axially, in the distal direction, with respect to the deshielder 33. It should be noted that the threads are designed to provoke such a translation in the distal direction, and that a translation in the proximal direction is impossible since the proximal end 53 of the sheath 51 is in contact with the distal end 9 of container 6.

This axial translation of the sheath 51 causes the axial translation of the needle shield 12 because of the radial wall 56 of the collar 55. During this movement, the needle shield 12 cannot rotate within the sheath 51. This can be achieved by using materials providing a high coefficient of friction between the sheath 51 and the needle shield 12 and a low coefficient of friction between the sheath 51 and the deshielder 33.

When the deshielder 33 has been rotated of half a turn, the sheath 51 extends beyond the distal end 37 of the deshielder 33 over a certain distance, and the bump 57 is located in line with the opposite slot 45b, 45a. The patient can go on turning the deshielder 33 about the axis 2 until the sheath 51 has completely come out of the deshielder 33. Preferably, the various components of the device 1 (in particular the pitch advance of the threads) are designed so that a rotational movement of 360° at most is sufficient to completely remove the needle shield 12. Alternatively, the patient can push the deshielder 33 axially (the bump 57 sliding into the slot 45b, 45a) in order to complete the removal. This pulling movement is far easier now that the contact surface between the needle 8 and the needle shield 12, and consequently the friction, has been greatly decreased. Means can be provided to limit the rotation of the deshielder 33 with respect to the housing 3 to around 180°, so that a patient can know when the bump 57 has reached the opposite slot 45b, 45a, i.e. when the deshielder 33 can be removed without requiring a great force.

The axially extending ribs 49 make the rotational movement easier for the patient, since they prevent the sliding of fingers on the external surface 48 of the deshielder 33. In a similar way, the radially extending ribs 50 make the pulling of the deshielder 33 easier. This axial pulling is also facilitated by the enlarged distal part 35 of the deshielder 33, which the fingers can grip.

The device 1 is provided to a user ready-to-use. i.e. the container 6 is filled with a predetermined dose of an injectable product, preferably a single dose thus providing a one-time use or disposable injection device. Once the deshielder 33 and the needle shield 12 have been removed, the patient places the device 1 against his/her skin at an injection site. As the device 1 is pressed against the user's skin, the safety shield 26 is caused to move in the proximal direction and into the body 21. Due to safety features of the device 1, a user cannot activate the device 1 (i.e., cause the container 6 to move from its initial position to its injection position) until the safety shield 26 is caused to move a predetermined distance in the proximal direction. Indeed, the container 6 is in its passive state as long as the safety shield 26 has not moved out of its first position.

With the device 1 pressed against his/her skin (and the safety shield 26 moved out of its first position in the proximal direction), the container 6 adopts its active state, and the user can activate the device 1 and begin an injection by pressing the push button 16. That will cause the container 6 to move from its initial position to its injection position, which also causes the needle 8 to pierce the user's skin. In addition, by pressing the push button 16 once, the inventive device 1 causes the injectable product to automatically be expelled from the container and into the user's skin. While the injection is being made or at the end of the injection process, the device 1 provides an audible indicator to the user of the status of the injection. For example, the device 1 may provide one or more audible clicks as the injection is being made—with the absence of a click indicating an end of the injection. In another example, a single click may indicate the end of the injection process.

Once the injection is complete, the user removes the device 1 from the injection site and the safety shield 26 is caused to automatically extend from the body 21 (i.e., lower body assembly 5) to cover the now-contaminated tip of the needle 8. Once the device 1 is removed from the injection site and the shield 26 is extended over the tip of the needle 8, the shield 26 locks in place and cannot thereafter be moved from its locked position in the proximal direction to expose the tip of the needle 8. The used device 1 is thus rendered safe for handling and disposal.

The device of the invention allow various possibilities for the patient to remove the deshielder, i.e. pulling off straight, twisting the deshielder, or a combination of these movements. In each case, the risk of generating rubber particles is greatly reduced.

What is claimed is:

1. A device for automatic injection of a product into an injection site, said device having a longitudinal axis and comprising:

a housing capable of receiving a container movable relative to said housing between an initial position, in which a tip of a needle provided on the container does not extend beyond a distal end of said housing, to an insertion position, distally spaced relative to said initial position and in which the tip of the needle extends beyond said distal end of said housing;

a needle shield for receiving said needle and in which the needle is embedded prior to use of said device;

a hollow sheath for receiving the needle shield therein with substantially no rotation therebetween, said sheath being configured to cooperatively engage the needle shield so that, while cooperatively engaged, displacement of said sheath in a distal direction results in distal displacement of the needle shield; and, a deshielder coupled to said needle shield and removably assembled to the distal part of the housing, said deshielder comprising a cylindrical through-hole having an axis substantially identical to the longitudinal axis, said sheath being mounted in the through-hole, wherein, said deshielder is rotatable relative to said distal part of the housing, said sheath and said deshielder being threadedly coupled so that a rotational movement of the deshielder about the device axis with respect to the housing causes an axial displacement of the needle shield in the distal direction with substantially no rotational movement of the needle shield with respect to the needle.

2. A device according to claim 1, wherein, with the sheath cooperatively engaging the needle shield, the needle shield is prevented from moving axially in a proximal direction relative to said sheath.

3. A device according to claim 1, wherein the deshielder is removably assembled to the distal part of the housing to allow axial displacement of the deshielder in the distal direction with respect to the housing with no possible simultaneous rotation of the deshielder, this axial displacement causing the axial removal of both the deshielder and the needle shield off the housing.

4. A device according to claim 1, further comprising at least one radially extending tongue projecting from a proximal end of the sheath and abutting onto the proximal end of the needle shield.

5. A device according to claim 4, wherein said at least are radially extending tongue abuts onto the distal end of the container prior to use of said device.

6. A device according to claim 1, wherein the deshielder comprises an annular housing, coaxial with the needle and having an internal diameter larger than the needle shield external diameter, said annular housing receiving a distal portion of the housing.

7. A device according to claim 6, wherein the annular housing has an internal diameter larger than the through-hole external diameter.

8. A device according to claim 6, wherein the annular housing comprises on one of its longitudinal walls a circular groove located in a plane substantially orthogonal to the device axis, and in that the distal portion of the housing comprises a bump intended to be inserted in said groove.

9. A device according to claim 8, wherein the annular housing further comprises on said longitudinal wall at least one axial slot the proximal end of which comes out at the proximal end of the deshielder annular housing and the distal end of which comes out into said circular groove, the bump provided on the housing distal portion being designed to slide into said slot.

10. A device according to claim 9, wherein said longitudinal wall of the annular housing comprises two diametrically opposed axial slots.

11. A device according to claim 10, wherein, prior to use of said device, the bump is located in the circular groove, at the distal end of one axial slot.

12. A device according to claim 1, wherein the deshielder comprises ergonomic means to make its removal off the housing easier for a patient.

13. A device according to claim 12, wherein the ergonomic means comprise ribs provided on the external surface of the deshielder and extending substantially axially and/or radially.

14. A device according to claim 12, wherein the deshielder has an enlarged distal part.

15. A device according to claim 1, further comprising a ring with breakable bridges connecting the housing and the deshielder prior to use of the device.

16. A device according to claim 1, wherein the threaded coupling between said sheath and said deshielder being designed so that a rotational movement of the deshielder about the device axis of 360° at most causes an axial displacement of the needle shield enough so that the needle is not embedded in the needle shield any more.

* * * * *